United States Patent [19]

Frosch et al.

[11] Patent Number: 5,440,039
[45] Date of Patent: Aug. 8, 1995

[54] PROCESS FOR THE CONTINUOUS REACTION OF CYANURIC FLUORIDE WITH AMINES AND A REACTOR FOR CARRYING OUT THIS PROCESS

[75] Inventors: Hans-Georg Frosch, Koeln; Manfred Hoppe, Kürten; Wolfgang Müllers, Bergisch Gladbach; Frank-Michael Stöhr, Odenthal, all of Germany

[73] Assignee: Bayer Aktiengesellschaft, Leverkusen, Germany

[21] Appl. No.: 697,862

[22] Filed: May 9, 1991

[30] Foreign Application Priority Data

May 19, 1990 [DE] Germany .................. 40 16 159.5

[51] Int. Cl.[6] ............................. C07D 251/54
[52] U.S. Cl. ........................................ 544/211
[58] Field of Search .......................... 544/211

[56] References Cited

U.S. PATENT DOCUMENTS

| 4,189,576 | 2/1980 | Fritzaltorfer et al. | 544/211 |
| 4,275,203 | 6/1981 | Hentschel et al. | 544/211 |
| 4,281,123 | 7/1981 | Hentschel et al. | 544/211 |
| 4,552,959 | 11/1985 | Punzar et al. | 544/190 |
| 4,678,852 | 7/1987 | Punzar et al. | 544/211 |
| 4,740,597 | 4/1988 | Franke et al. | 544/211 |

Primary Examiner—Yogendra N. Gupta
Attorney, Agent, or Firm—Sprung Horn Kramer & Woods

[57] ABSTRACT

The yield and purity of the condensate obtained in the reaction of cyanuric fluoride with an aqueous amine solution is improved by introducing the reactants into a reactor (1) at a differential rate which results in intensive mixing and substantially completing the reaction in the reactor (1) with no back-mixing, the reactor (1) preferably being a tube (1) into which one nozzle (2) opens axially and one or more nozzle(s) (4) open(s) concentrically thereto.

7 Claims, 1 Drawing Sheet

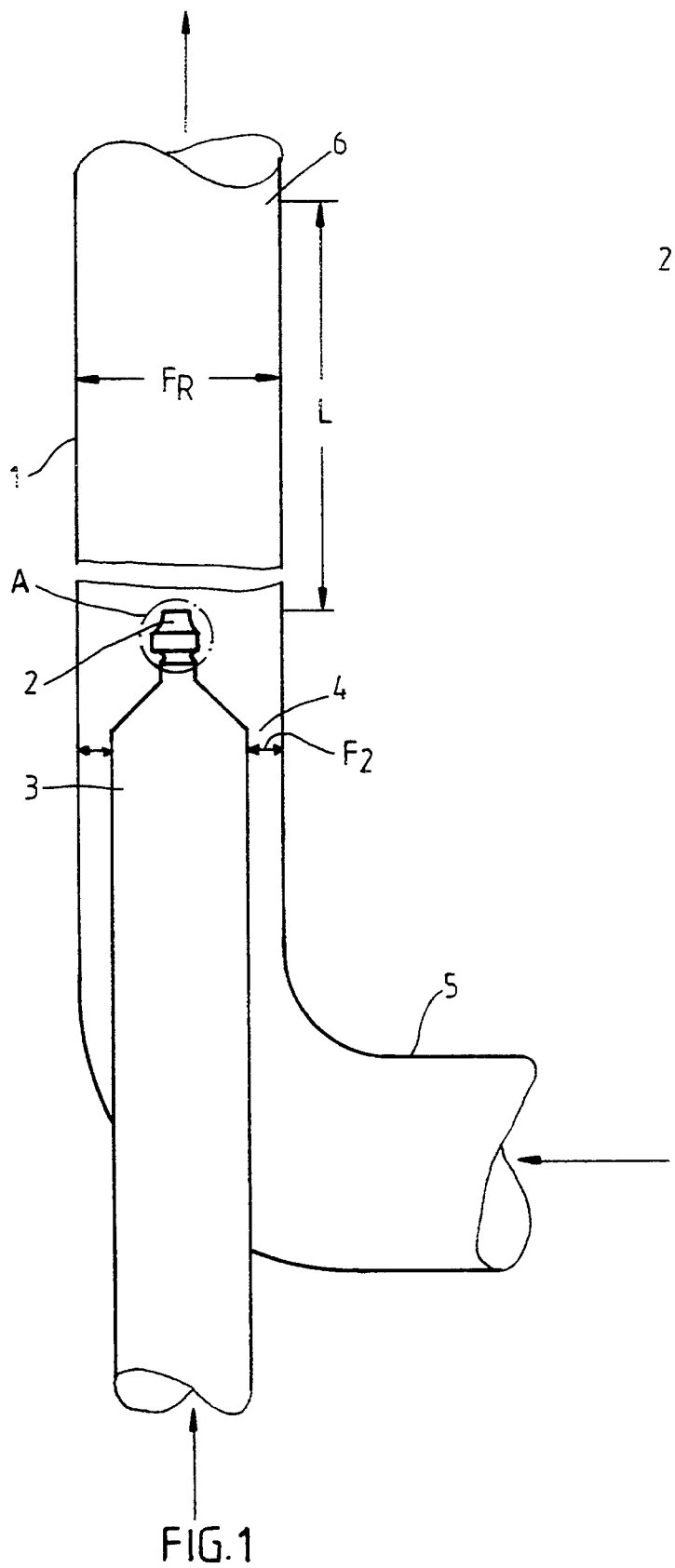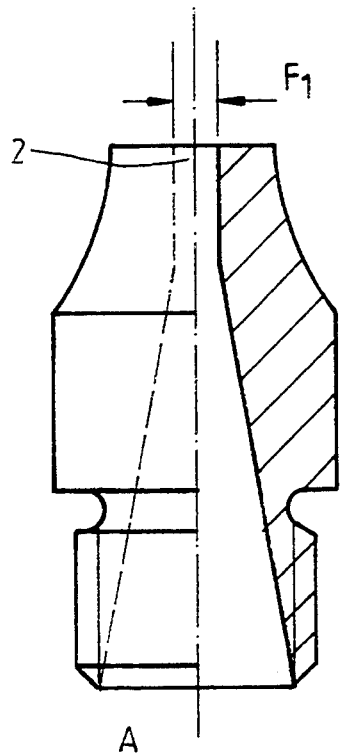

PROCESS FOR THE CONTINUOUS REACTION OF CYANURIC FLUORIDE WITH AMINES AND A REACTOR FOR CARRYING OUT THIS PROCESS

This invention relates to a process for the continuous reaction of cyanuric fluoride with amines, in which cyanuric fluoride and an aqueous amine solution are introduced into a reactor, and to a reactor for carrying out this process.

DE-C2-2 746 109 describes a process for the continuous reaction of cyanuric fluoride with aminobenzene sulfonic acids or aminonaphthalene sulfonic acids, in which the reactor used is an "ideal tank" through which the reactants flow continuously with complete back-mixing. However, this known process can only be applied to a limited extent to the reaction of cyanuric fluoride with aminonaphthol sulfonic acids because considerable quantities of secondary products are formed in this case.

In addition, EP-A2-0 172 790 describes a process for the continuous reaction of cyanuric fluoride with aminobenzene sulfonic acids or aminonaphthalene sulfonic acids, in which cyanuric fluoride and an aqueous solution of the amine are introduced simultaneously and continuously into a first reactor and are intensively mixed therein and the resulting reaction mixture is subsequently introduced into a second reactor in which only minimal back-mixing, but thorough radial mixing occurs and in which the reaction is completed.

However, this process has certain disadvantages, namely that a second reactor is required and that the amount of secondary products formed, although reduced in relation to the process described in DE-C2-2 746 109, is still unsatisfactorily high.

The problem addressed by the present invention was to provide a process and a reactor for the continuous reaction of cyanuric fluoride with amines containing sulfone groups and chromophores, more particularly aminonaphthol sulfonic acids, to amino condensates, i.e. compounds obtained by reaction of 1 mol cyanuric fluoride with 1 mol amine, which would produce an improved yield and/or purity.

According to the invention, the solution to this problem is characterized in that the educts are introduced simultaneously and continuously into the reactor at different rates, intensive mixing is produced by the difference between the flow rates and the reaction is substantially completed in this reactor with no back-mixing.

Surprisingly, a conversion of at least 95% can be obtained in a single reaction step by this process.

In one particular embodiment of the new process, the cyanuric fluoride flows into the reactor at a Reynolds number of at least 10,000 and preferably of at least 15,000 while the aqueous amine solution flows into the reactor at a Reynolds number of at least 2,500 and preferably of at least 5,000, the difference between the flow rates of the cyanuric fluoride stream and the amine solution stream being at least 20 m/s and preferably at least 40 m/s.

These measures guarantee particularly intensive mixing over a very short distance with no back-flow.

The ratio of the reactor cross-section to the inflow cross-section of the cyanuric fluoride stream is preferably from 225 to 40,000 and more preferably from 700 to 12,000.

This adaptation of the cross-sectional ratio to the mass flow ratio optimizes the backflow-free mixing of the reactants.

The residence time in the reactor is preferably at most 5 s and, more particularly, from 0.2 to 2 s.

It has been found that this residence time is sufficient for an almost complete reaction.

In another preferred embodiment of the new process, the reaction is carried out at temperatures of 0° to 50° C. and preferably at temperatures of 0° to 20° C.

The new process is particularly suitable for the reaction of 2,4,6-trifluoro-s-triazine with sulfo-containing anilines and naphthylamines or with sulfo-containing aminonaphthols and for the reaction of 2,4,6-trifluoro-s-triazine with amines containing chromophores.

It is of particular advantage to use a tube reactor into which the cyanuric fluoride is introduced in the form of an axial jet while the amine solution is introduced as a concentric jet at a differential rate which ensures intensive mixing, the reaction being substantially completed in this reactor.

Where this procedure is adopted, intensive mass transfer takes place at the interface between the two jets.

Surprisingly, the reaction products of 1 mol aminonaphthol sulfonic acid with 1 mol cyanuric fluoride are also obtained in high yields and purities where this procedure is adopted. In many cases, the process according to the invention is also better than known processes for the reaction of aminobenzene or aminonaphthalene sulfonic acids or chromophore-containing amines with cyanuric fluoride.

However, the process according to the invention may also be carried out with ammonia or aliphatic amines, for example ethanolamine, morpholine or taurine. However, aromatic amines containing sulfo groups and chromophore-containing amines are preferably used, the negative charges of the sulfo groups also being equalized by quaternary, more particularly aliphatic, ammonium ions.

Examples of suitable aromatic amines containing sulfo groups are 1-aminobenzene-2-sulfonic acid, 1-aminobenzene-3-sulfonic acid, 1-aminobenzene-4-sulfonic acid, 1-amino-4-methylbenzene-3-sulfonic acid, 1-amino-4-methoxybenzene-3-sulfonic acid, 1-amino-2-methylbenzene-4-sulfonic acid, 1-amino-3-methylbenzene-4-sulfonic acid, 1-aminobenzene-3,5-disulfonic acid, 2-amino-5-sulfobenzoic acid, 1-aminonaphthalene-4-sulfonic acid, 1-aminonaphthalene-5-sulfonic acid, 1-aminonaphthalene-6-sulfonic acid, 2-aminonaphthalene-5-sulfonic acid, 2-aminonaphthalene-7-sulfonic acid, 2-aminonaphthalene-4,8-disulfonic acid, 2-aminonaphthalene-5,7-disulfonic acid, 1,4-diaminobenzene-2,5-disulfonic acid, 1,3-diaminobenzene-4-sulfonic acid, 1,4-diaminobenzene-2-sulfonic acid, 1,3-diaminobenzene-4,6-disulfonic acid, 1-amino-5-hydroxynaphthalene-7-sulfonic acid, 1-amino-8-hydroxynaphthalene-4-sulfonic acid, 1-amino-8-hydroxynaphthalene-3-sulfonic acid, 1-amino-8-hydroxynaphthalene-5-sulfonic acid, 2-amino-5-hydroxynaphthalene-7-sulfonic acid, 2-amino-6-hydroxynaphthalene-8-sulfonic acid, 2-amino-8-hydroxynaphthalene-6-sulfonic acid, 2-methylamino-5-hydroxynaphthalene-7-sulfonic acid, 2-ethylamino-5-hydroxynaphthalene-7-sulfonic acid, 2-methylamino-8-hydroxynaphthalene-6-sulfonic acid, 2-ethylamino-8-hydroxynaphthalene-6-sulfonic acid, 1-amino-6-hydroxynaphthalene-3,8-disulfonic acid, 1-amino-8-hydroxynaphthalene-3,6-disulfonic acid, 1- amino-8-hydroxynaphthalene-2,4-disulfonic acid, 1-amino-8-hydroxynaphthalene-4,6-disulfonic acid, 1-amino-8-hydroxynaphthalene-3,5-disulfonic acid, 2-amino-5-hydroxynaphthalene-7,1-disulfonic acid and 2-amino-8-hydroxynaphthalene-3,6-disulfonic acid.

The process according to the invention is particularly suitable for the reaction of cyanuric fluoride with 2-amino-5-hydroxynaphthalene-7-sulfonic acid, 2-amino-8-hydroxynaphthalene-6-sulfonic acid, 1-amino-8-hydroxynaphthalene-4,6-disulfonic acid or, above all, 1-amino-8-hydroxynaphthalene-3,6-disulfonic acid or 1-aminobenzene-3-sulfonic acid.

The amines containing sulfo groups or chromophores are used in the form of aqueous solutions. The cyanuric fluoride may be used in a relatively large excess. It is best to use the cyanuric fluoride and the amine in a molar ratio of 0.8:1 to 1.5:1, preferably in a molar ratio of 1:1 to 1.2:1 and, more preferably, in a molar ratio of 1:1 to 1.08:1.

A buffer substance is preferably added to the amine solution to maintain a pH value in the range from 1 to 8 and preferably in the range from 3 to 5, depending on the buffer substance, during the reaction. Suitable buffer substances are, for example, alkali metal fluorides, borates and phosphates, more particularly NaF. These buffer substances are generally used in a quantity of 0.2 to 2 mol and preferably in a quantity of 0.4 to 1.2 mol per mol amine.

The resulting reaction products of 1 mol amine and 1 mol cyanuric fluoride may be isolated, although they are preferably further processed without isolation, for example to reactive dyes, by reaction with another amine or a dye containing amino groups or by reaction with an aromatic amine and subsequent coupling with a diazonium compound. This further processing may be carried out discontinuously or continuously in known manner.

In many cases, the process according to the invention gives the condensates of cyanuric fluoride and aromatic amines containing sulfo groups or chromophores in distinctly higher purity than conventional processes. This has a positive effect on the quality of the reactive dyes produced from the condensates because the condensates are normally further processed without purification.

The new process may be carried out in various reactors providing they allow intensive mixing and providing the reaction mixture is able to flow through continuously without any back-mixing.

One reactor which has proved to be particularly suitable for carrying out the new process is a tube into which one nozzle opens axially and one or more nozzles open concentrically thereto for introducing the educts.

In one particular embodiment, the outflow direction of the concentrically opening nozzle(s) is inclined at 45° to 90° to the outflow direction of the axial nozzle. This provides for particularly intensive mass transfer between the two educt streams.

The tube continues in the direction of flow and, after the reaction zone, is used to dissipate the reaction product, the reaction zone which begins immediately where the nozzles open covering only a short distance. A two-component nozzle or a central nozzle and a surrounding annular gap are particularly suitable for introducing the reactants, the cyanuric fluoride being introduced centrally and the aqueous amine solution concentrically thereto.

The preferred new reactor is described in detail in the following with reference to the accompanying schematic drawings, wherein:

FIG. 1 is a section through the reactor.

FIG. 2 shows the nozzle (detail A), half in section, on an enlarged scale.

A feed pipe 3 for 2,4,6-trifluoro-s-triazine (cyanuric fluoride) opens axially into a reaction tube 1 having a circular cross-section $F_R$ of 80 mm$^2$ through a nozzle 2 having a cross-section $F_1$ of 0.03 mm$^2$. The feed pipe 3 is concentrically surrounded by an annular nozzle 4 having a cross-section $F_2$ of 64 mm$^2$ which is connected to a feed pipe 5 for an aqueous amine solution. The length L of the reaction zone is the product of the residence time of 5 s and preferably 2 s and the overall flow rate of cyanuric fluoride and amine solution. The following tube section 6 is used to transport the reaction product.

Instead of an annular nozzle 4, several individual nozzles or nozzle openings may be distributed around the circumference.

EXAMPLE 1

5.4 l/h cyanuric fluoride having a temperature of approximately 20° C. and a Reynolds number of 16,000 and 225 l/h of an aqueous solution at 0° C. containing 0.26 mol/l 1-amino-8-hydroxynaphthalene-3,6-disulfonic acid, 0.1 mol/l NaF and 0.26 mol/l NaOH, Reynolds number 8,000, are introduced simultaneously and continuously into a reactor of the type shown in FIG. 1 through separate feed pipes 3 and 5 or nozzle openings 2 and 4. The ratio between the flow cross-section $F_R$ of the reactor 2 and the flow cross-section $F_1$ of the nozzle 2 is 2.660.

The cyanuric fluoride is sprayed into the aqueous solution with a difference in flow rate of 49 m/s. The residence time in the reaction zone is approximately 0.7 s, i.e. the reaction is substantially completed within this time.

The reaction mixture, which leaves the reaction zone L (L=570 mm) with a temperature of 9° C., contains the compound

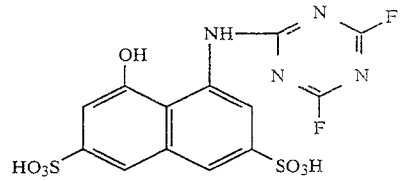

in a yield of 93 ±2%, based on the 1-amino-8-hydroxynaphthalene-3,6-disulfonic acid used.

By way of comparison, a yield of only 85% is obtained in this reaction stage using the process according to EP-A-172 790 (page 6, top).

The reaction mixture obtained is introduced into a stirred tank in which it is converted into a red reactive dye by the following procedure:

A solution containing 1 mol p-chloraniline, 500 ml water and 100 ml 32% hydrochloric acid is added to the reaction mixture per mol of the condensate described above and a pH value of 6.0 is established over a period of 10 to 20 minutes with 20% NaOH.

The solution obtained is added to a diazonium salt suspension at 0° to 5° C. which has been obtained by diazotization of 1 mol 2-naphthylamine-1,5-disulfonic acid by the standard method. A pH value of 7.5 is established at max. 10° C. by the addition with intensive stirring of 30% sodium hydroxide, followed by stirring for 1 hour at pH 7.5/10° C.

A dye corresponding to the following formula is obtained:

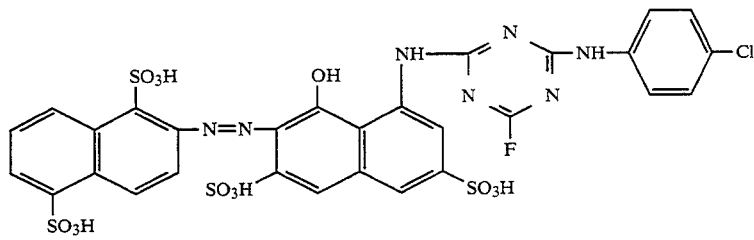

with which cellulose material can be dyed shades of red.

EXAMPLE 2

5.4 l/h cyanuric fluoride having a temperature of approximately 20° C. and a Reynolds number of 16,000 and 225 l/h of an aqueous solution at 0° C. containing 0.26 mol/l 1-amino-8-hydroxynaphthalene-3,6-disulfonic acid, 0.1 mol/l NaF and 0.26 mol/l morpholine, Reynolds number 8,000, are introduced simultaneously and continuously into a reactor of the type shown in FIG. 1 through separate feed pipes 3 and 5 or nozzle openings 2 and 4. The ratio between the flow cross-section $F_R$ of the reactor 1 and the flow cross-section $F_1$ of the nozzle 2 is 2.660.

The cyanuric fluoride is sprayed into the aqueous solution with a difference in flow rate of 49 m/s. The residence time in the reactor 1 is 0.7 s, corresponding to a length L of 570 mm.

The reaction mixture, which leaves the reactor with a temperature of 9° C., contains the compound

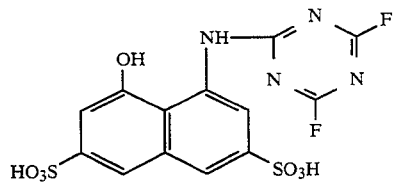

in the form of the morpholine salt. The yield comprises 93 ±2%.

The coupling component

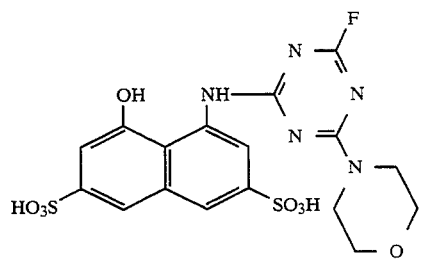

is obtained by adjusting the pH value to 7 with LiOH and is further processed by diazotization as in Example 1 to form a dye corresponding to the following formula

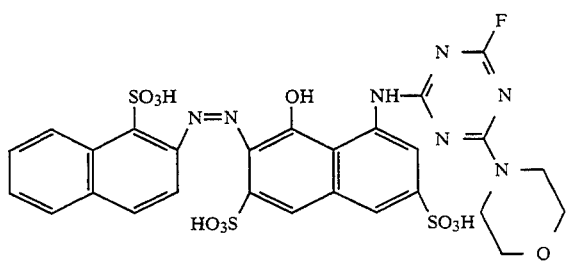

The dye colors cellulose shades of bluish-red with very high wet fastness.

We claim:

1. A process for the continuous reaction of cyanuric fluorides with amines in which cyanuric fluoride and an aqueous amine solution are introduced into a reactor (1) and the reaction product is subsequently removed, characterized in that the reactants are introduced simultaneously and continuously into the reactor (1) at different rates, intensive mixing is produced by the difference between the flow rates and the reaction is substantially completed in this reactor (1) with no back-mixing.

2. A process as claimed in claim 1, characterized in that the cyanuric fluoride flows into the reactor (1) at a Reynolds number of at least 10,000 while the aqueous amine solution flows into the reactor (1) at a Reynolds number of at least 2,500, the difference between the flow rates of the cyanuric fluoride stream and the amine solution stream being at least 20 m/s and preferably at least 40 m/s.

3. A process as claimed in claim 1, characterized in that the ratio of the reactor cross-section $F_R$ to the inflow cross-section $F_1$ of the cyanuric fluoride stream is kept at 225 to 40,000 and preferably at 700 to 12,000.

4. A process as claimed in claim 1, characterized, in that the residence time in the reactor (1) is at most 5 s.

5. A process as claimed in claim 1, characterized in that the reaction is carried out at temperatures of 0° to 50° C.

6. A process as claimed in claim 1, characterized in that 2,4,6-trifluoro-s-triazine is reacted with anilines and naphthylamines containing sulfo groups or with aminonaphthols containing sulfo groups.

7. A process as claimed in claim 1, characterized in that 2,4,6-trifluoro-s-triazine is reacted with amines containing chromophores.

* * * * *